United States Patent [19]

Jordan et al.

[11] Patent Number: Plant 6,589

[45] Date of Patent: Feb. 7, 1989

[54] CHRYSANTHEMUM PLANT NAMED GOLDEN GEOS

[75] Inventors: Christine Jordan, Tenerife, Canary Islands, Spain; Marie Satory, Hamburg, Fed. Rep. of Germany

[73] Assignee: Ball Pan Am Plant Co., Parrish, Fla.

[21] Appl. No.: 70,728

[22] Filed: Jul. 7, 1987

[51] Int. Cl.[4] ..... A01H 5/00

[52] U.S. Cl. ..... Plt./78

[58] Field of Search ..... Plt./78

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A cultivar of Chrysanthemum named Golden Geos having bright yellow flower color, compact growth habit, nine-week response, fully double flower with no disc florets, high floret count thereby producing a dense flower, excellent low light performance, and superior keeping and shipping qualities.

1 Drawing Sheet

The present invention comprises a new and distinct cultivar of Chrysanthemum, botanically known as *Chrysanthemum morifolium,* Ramat., and referred to by the cultivar name Golden Geos.

Golden Geos is a product of a radiation-induced mutation program which had the primary objectives of creating new Chrysanthemum cultivars with decorative type flowers and excellent pot plant performance under low light winter conditions.

Golden Geos was originated from an induced mutation of Geos in a controlled program in Ahrensburg-/Holstein, Germany in 1980. Golden Geos was discovered and selected by Christine Jordan and Marie Savory as a mutation from a block of flowering plants of Geos in the greenhouses of Bundesforschungsanstalt Fuer Gartenbauliche Pflanzenvzvechtung in 1980 in a controlled environment in Ahrensburg/Holstein, Germany.

The first act of asexual reproduction of Golden Geos was accomplished when vegetative cuttings were taken from the initial selection on Jan. 15, 1981 by applicants in a controlled environment in Ahrensburg/Holstein, Germany.

Horticultural examination of selected units initiated Apr. 15, 1981 by applicants has demonstrated that the combination of characteristics as herein disclosed for Golden Geos are firmly fixed and are retained through successive generations of asexual reproduction.

The following traits have been repeatedly observed and are determined to be basic characteristics of Golden Geos, which, in combination, distinguish this Chrysanthemum as a new and distinct cultivar:

1. Nine-week response period.
2. Compact growth habit.
3. Bright yellow flower color.
4. Fully double flower with no disc florets present.
5. Diameter of capitulum 8–13 cm.
6. Florets range up to 55 mm at outer edge of capitulum (fully expanded petals).
7. Approximately 350 florets per capitulum, providing a very dense flower.
8. Superior keeping and shipping qualities.
9. Finished pot height of 25–30 cm from top edge of the pot, depending upon growing conditions.
10. Excellent low light performance.

Golden Geos has not been observed under all possible environmental conditions. The phenotype may vary significantly with variations in environment such as temperature, light intensity, and day length.

The following observations, measurements and comparisons describe plants grown in Parrish, Fla. under greenhouse conditions which approximate those generally used in commercial practice.

Of the many commercial cultivars known to the present inventors, the most similar in comparison to Golden Geos is Bright Golden Anne. In comparison to Bright Golden Anne, Golden Geos has a more compact habit and is one week earlier (9 weeks vs. 10 weeks). In addition, Golden Geos has 6–6 breaks per plant while Bright Golden Anne has 3–4, making Golden Geos relatively more floriferous. The flower form and color are similar to those same characteristics of Bright Golden Anne.

In comparison to the parent cultivar Geos, the latter is white and slightly taller in growth habit.

The accompanying photographic drawing shows typical inflorescence and foliage characteristics of Golden Geos. The drawing comprises a black and white photograph, with one flower being colored to depict the true flower color of Golden Geos.

In the following description, color references are made to the Royal Horticultural Society Colour Chart. The color values were determined at 2:00 p.m. on July 21, 1986 under fluorescent light at Parrish, Fla.

Classification:

*Botanical.*—*Chrysanthemum morifolium,* Ramat., cv. Golden Geos.

*Commercial.*—Decorative pot mum.

INFLORESCENCE

A. Capitulum:

*Form.*—Flat.

*Type.*—Double.

*Diameter across face.*—8–13 cm.

B. Corolla of ray florets:

*Color (general tonality from a distance of three meters).*—Yellow.

*Color (upper surface).*—9B.

*Color (under surface).*—9A.

C. Corolla of disc florets: None.

D. Reproductive organs:

*Androecium.*—None.

*Gynoecium.*—Present in all ray florets.

PLANT

A. General appearance:

*Height.*—25–30 cm from the top edge of the pot.

B. Foliage:

*Color* (*upper surface*).—147A.

*Color* (*under surface*).—147B.

*Shape.*—Ovate, deeply lobed and slightly serrage margins.

We claim:

1. A new and distinctive cultivar of Chrysanthemum named Golden Geos, as illustrated and described.

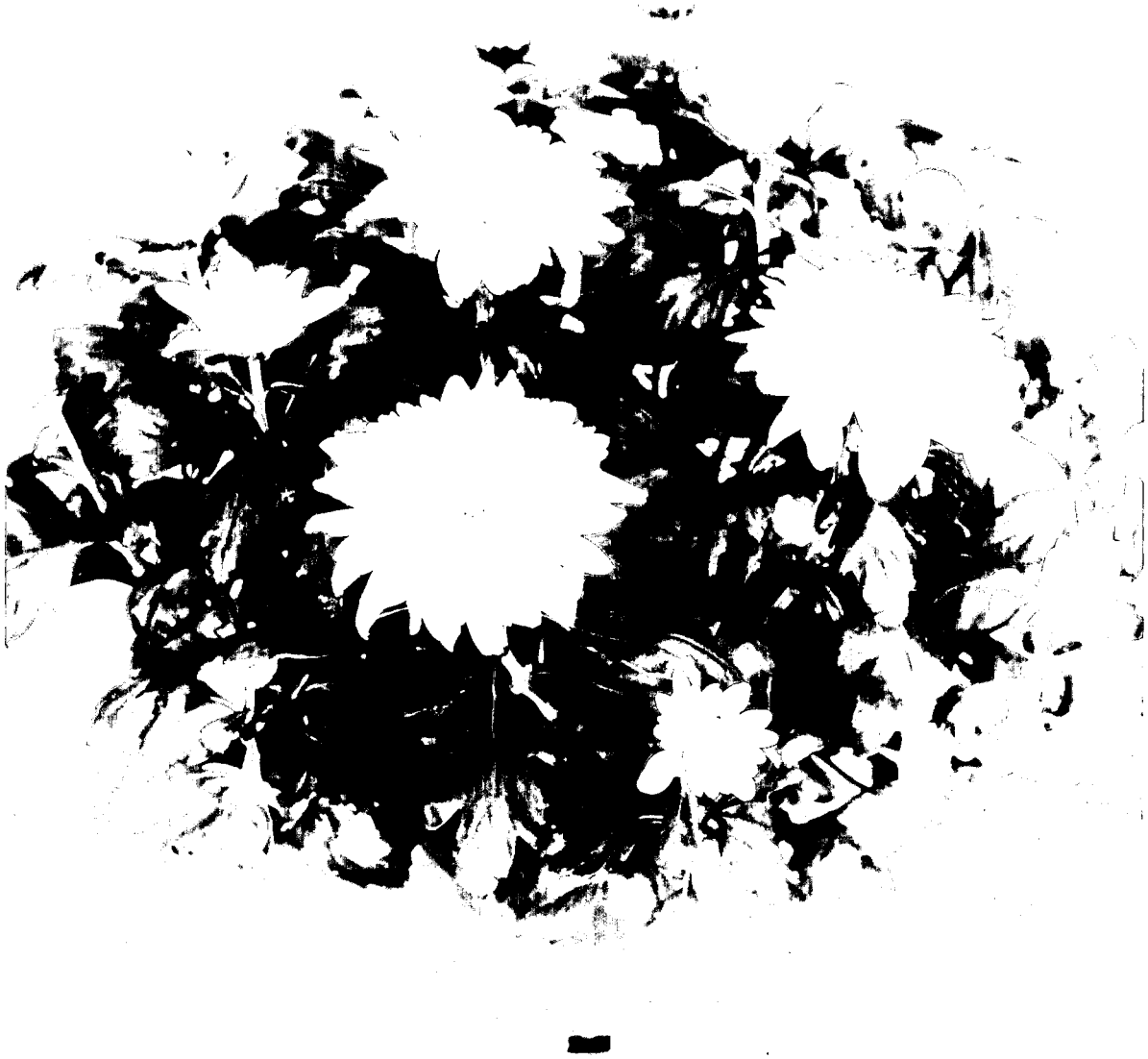

* * * * *